United States Patent [19]

Karlsson

[11] Patent Number: 5,753,518
[45] Date of Patent: May 19, 1998

[54] METHOD OF DETERMINING AFFINITY AND KINETIC PROPERTIES

[75] Inventor: Robert Karlsson, Uppsala, Sweden

[73] Assignee: Pharmacia AB, Stockholm, Sweden

[21] Appl. No.: 553,413

[22] PCT Filed: May 24, 1994

[86] PCT No.: PCT/SE94/00480

§ 371 Date: Nov. 22, 1995

§ 102(e) Date: Nov. 22, 1995

[87] PCT Pub. No.: WO94/28416

PCT Pub. Date: Dec. 8, 1994

[30] Foreign Application Priority Data

May 24, 1993 [SE] Sweden .................................. 9301755

[51] Int. Cl.$^6$ .................................................. G01N 33/557
[52] U.S. Cl. ............... 436/517; 204/403; 422/57; 422/68.1; 422/82.01; 422/82.05; 422/82.08; 422/82.09; 422/82.11; 435/7.2; 435/287.1; 435/287.2; 435/288.7; 435/808; 436/518; 436/527; 436/805; 436/806; 310/311; 310/312
[58] Field of Search ........................ 204/400, 403, 204/422; 422/57, 68.1, 82.01, 82.05, 82.08, 82.09, 82.11, 98; 435/7.2, 287.1, 287.2, 288.7, 808; 436/517, 518, 149, 806, 527, 805; 310/311, 312

[56] References Cited

FOREIGN PATENT DOCUMENTS

| 0276142 | 7/1988 | European Pat. Off. . |
| WO90/05305 | 5/1990 | WIPO . |
| WO90/05306 | 5/1990 | WIPO . |

OTHER PUBLICATIONS

Kim R. Rogers et al "Biosensors & Bioelectronics", vol. 6, 1991 pp. 507–516.
Robert Karlsson et al "Journal of Immunological Methods" 145 (1991) pp. 229–240.

*Primary Examiner*—Christopher L. Chin
*Attorney, Agent, or Firm*—Birch, Stewart, Kolasch & Birch, LLP

[57] ABSTRACT

A method of determining the affinity and kinetic properties of low molecular weight ligands for their interaction with a common receptor comprises the steps of immobilizing the receptor on a sensing structure, mixing in known proportions each ligand with a ligand analogue the response of which on the sensing structure is substantially higher than that of the low molecular weight ligands, contacting each mixture with the sensing structure and measuring the response, and comparing the response of each mixture with that of the ligand analogue alone, the distortion of the ligand analogue response being representative of the affinity and kinetic properties of the ligand.

12 Claims, 6 Drawing Sheets

METHOD OF DETERMINING AFFINITY AND KINETIC PROPERTIES

The present invention relates to the determination of the affinity and kinetic properties of particularly low molecular weight compounds with regard to their interactions with a receptor molecule.

Ligand-receptor interactions are usually characterized in the terms of the binding affinity. Determination of rate constants would be helpful to characterize the interaction, but unfortunately only a few methods are available where the kinetic properties of the interaction can be directly visualized. One such method, which has recently been described (Karlsson R. et al., J. Immunol. Meth. 145, 229–240, 1991), uses mass sensitive detection and a flow system for direct kinetic analysis of ligands interacting with their immobilized receptors at a sensor surface. However, this method is restricted to the study of high molecular weight ligands, the increase of mass on the sensor surface in the case of low molecular weight components ($M_w$<approx. 3000 Da) which interact with an immobilized receptor being too small to be accurately measured.

EP-A-276 142 discloses a method of quantitatively measuring, on a surface of an optical structure capable of exhibiting surface plasmon resonance (SPR), small molecules, such as drugs and hormones, using a competitive assay format. The method is characterized in that the sample antigen will compete with the same antigen (or an antigen analogue) coupled to a comparatively large (optical thickness enhancing) "label particle", such as a latex particle, for the binding to an immobilized receptor. The amount of labelled antigen bound will then be inversely proportional to the concentration of antigen in the sample.

Rogers, K. R., et al., Biosensors & Bioelectronics 6 (1991) 507–516 describes the use of fluorescence-labelled ligands to determine the number of free sites on a receptor bound to a fibre-optical biosensor. To determine the affinity for the reaction of a non-labelled ligand with the receptor, the receptor is incubated with non-labelled ligand, a fluorescence-labelled ligand is added and the fluorescence measured, and the measured fluorescence signal is compared with that obtained when the receptor is reacted directly with the fluorescence-labelled ligand. When the procedure is repeated with a number of concentrations of non-labeled ligand, the affinity constant for the interaction between the non-labeled ligand and the receptor may be calculated.

In accordance with the present invention, it has now been found that the lack of sensitivity of mass-sensing methods to accurately detect low molecular molecules when the size of the receptor molecule is much larger than the molecule to be detected may be advantageously utilized to compare by competitive kinetics the affinity and kinetic properties of different low molecular weight components interacting with the same receptor, using an approach similar to that used for the concentration measurements in EP-A-276 142 above.

According to this novel concept of competitive kinetics, two ligands are allowed to react simultaneously with the binding site of a common immobilised receptor. One of the ligands is of high molecular weight and the other is one of low molecular weight. The progress of the binding interaction with the receptor is studied by recording the binding curves (plotting of the detector response versus time) for, on one hand, each ligand alone and, on the other hand, when the high molecular weight ligand and the low molecular weight ligand compete for the binding site of the receptor. In the latter case, both ligands bind to the receptor but almost the entire signal will be due to the binding of the high molecular weight component. The binding of the low molecular weight component is instead seen as a distortion of the binding curve obtained with the high molecular weight ligand alone. The change in shape and in position of the binding curve obtained under competing conditions thus reflects the kinetic and affinity properties of the low molecular weight ligand-receptor interaction.

By proceeding in this way, for example, low molecular weight ligands may be affinity ranked relative to each other by studying their influence on the binding of a high molecular ligand analogue to the same receptor. This may be favourably applied in inter alia drug screening.

The present invention therefore generally relates to a novel method of determining at least the relative affinities and kinetic properties of low molecular weight ligands for their interactions with a common receptor, which method is characterized by immobilizing the receptor on a sensing structure, mixing in known proportions each low molecular weight ligand with a ligand analogue the response of which on the sensing structure is substantially higher than that of the low molecular weight ligands, contacting each mixture with the sensing structure and measuring the response, and comparing the response of each mixture with that of the ligand analogue alone, the distortion of the ligand analogue response being representative of the affinity and kinetic properties of the ligand.

By the expression "substantially higher" with regard to the ligand analogue response is to be understood that the contribution of the ligand analogue response in a mixture with a low molecular weight ligand should represent the major part of the response of the mixture. Preferably, the response of the ligand analogue is from about 20 times that of low molecular weight ligand (i.e. about 95%) to, say, about 100 times that of low molecular weight ligand. Such relatively higher response of the ligand analogue may be inherent in the basic molecule per se or may be provided by a species bound to the basic ligand analogue molecule.

An advantageous feature of the invention is that it is not necessary to study the binding curve up to steady state, or equilibrium, as is the case in the concentration measurement proposed in the above EP-A-276 142, but the initial part of the binding curve is sufficient. It is readily seen that a considerable amount of time will be saved thereby.

Preferably, however, also the dissociation phase is studied, i.e. the dissociation of the bound ligands from the sensor surface when the surface is no longer contacted with the ligand solution.

The low molecular weight ligand may be a drug or a potential drug reacting with its receptor, or it may be the binding part obtained from a larger molecule interacting with the binding partner of the parent molecule.

In a preferred embodiment, the ligand analogue is a high molecular weight molecule.

Such high molecular weight ligand analogue may be an antibody or the binding part of an antibody, but preferably the high molecular weight ligand is a conjugate of one of the low molecular ligands and a high molecular weight component. "High molecular weight", which term is to be interpreted broadly, may for the present purposes be from, say, about 5000 Dalton to about 1000×the molecular weight of the low molecular weight component. In the case where the low molecular weight ligand is obtained from a larger molecule (the low molecular weight component being, for example, a peptide or an oligonucleotide), the high molecular weight ligand may be the parent molecule.

Preferably, the high molecular weight ligand reacts in a one-to-one fashion with the immobilised binding partner, the interaction preferably being characterized by a high dissociation rate constant ($0.001 < k_{diss} < 0.1$).

The low molecular weight ligands and the ligand analogue are preferably introduced over the sensor surface in such a way that for each component the concentration may be regarded as constant over time, and thereby pseudo first order reaction kinetics may be assumed.

While a stationary assay format may be used, it is preferred to use a dynamic format, the low molecular weight ligands and the ligand analogues, respectively, being introduced over the sensor surface in a fluid flow.

For screening purposes, the low molecular weight ligands and the ligand analogues may be presented simultaneously onto an array of sensor surfaces (such arrays of sensor surfaces being known per se in the art) with either different receptors or different amounts of a single receptor immobilised.

The invention is generally applicable to those detection methods where the parameter being measured is generated from both the ligand and the ligand analogue, such as e.g. mass, charge, dielectric constant etc. Among these methods are, for example, mass detecting methods, such as piezoelectric, optical and thermo-optical methods, and electrochemical methods, such as potentiometric, conductometric and amperometric methods.

Among optical methods may particularly be mentioned those that detect mass surface concentration, such as reflection-optical methods, including both internal and external reflection methods, e.g. ellipsometry and evanescent wave spectroscopy (EWS), the latter including surface plasmon resonance spectroscopy (SPRS), Brewster angle reflectometry, critical angle reflectometry, frustrated total reflection (FTR), evanescent wave ellipsometry, scattered total internal reflection (STIR), optical waveguide sensors, etc.

SPR-based detection methods have attracted much attention lately. The phenomenon of SPR is well known. In brief, SPR is observed as a dip in intensity of light reflected at a specific angle from the interface between an optically transparent material, e.g. glass, and a thin metal film, usually silver or gold, and depends on among other factors the refractive index of the medium (e.g. a sample solution) close to the metal surface. A change of refractive index at the metal surface, such as by the adsorption or binding of material thereto, will cause a corresponding shift in the angle at which SPR occurs. To couple the light to the interface such that SPR arises, two alternative arrangements are used, either a metallized diffraction grating (Wood's effect), or a metallized glass prism or a prism in optical contact with a metallized glass substrate (Kretschmann effect). For further details on SPR, reference is made to our WO 90/05295. In an SPR-based assay, a receptor is bound to the metal surface, and the interaction thereof with a ligand in a solution in contact with the surface is monitored.

A commercial SPR-based biosensor system based on the Kretschmann effect (BIAcore™ system, supplied by Pharmacia Biosensor AB, Uppsala, Sweden) was used in the following non-limiting examples which illustrate the method of the invention.

EXAMPLE 1

Preparation of Sensor Surfaces

A continuous flow of HBS (10 mM Hepes with 0.15M NaCl, 3.4 mM EDTA and 0.05% surfactant P20 at pH 7.4) was maintained over a BIAcore™ sensor chip CM5 (a gold-plated glass slide supporting a carboxymethyldextran layer via a monolayer of long-chain hydrocarbons; supplied by Pharmacia Biosensor AB, Uppsala, Sweden). The carboxylated matrix on the sensor surface was activated by a three-minute injection of a solution containing 0.2M N-ethyl-N'-(3-diethylaminopropyl)carbodiimide (EDC) and 0.05M N-hydroxysuccinimide (NHS). 100 µg/ml of rabbit anti-mouse Fc (RAMF$_c$) antibodies (Pharmacia Biosensor AB, Uppsala, Sweden) in 10 mM acetate buffer, pH 4.75, were then injected followed by a pulse of ethanolamine-hydrochloride, pH 8.5, to block remaining NHS-ester groups.

Binding of Anti-p24-Mab to the Sensor Surface and Kinetic Analysis of p24 Ligand Interaction With the above prepared sensor surface docked into the BIAcore™ instrument, a solution of purified monoclonal anti-p24 antibody (Pharmacia Diagnostics AB, Uppsala, Sweden), hereinafter referred to as Mab 7, was injected, the anti-p24 monoclonal antibody thereby being captured by the immobilized RAMFc. Different solutions of HIV core protein p24 (Pharmacia Genetic Engineering, San Diego, USA), varying in concentration from 18.75 to 300 nM, were then injected and the binding curves, relative response in resonance units (RU) versus time in seconds, were recorded (1 RU corresponds to a mass change, caused by the binding of a protein, on the sensor surface of about 1 pg/mm$^2$; Stenberg, E., et al., J. Colloid and Interface Sci. 143 (1991) 513–526).

Figure 1:
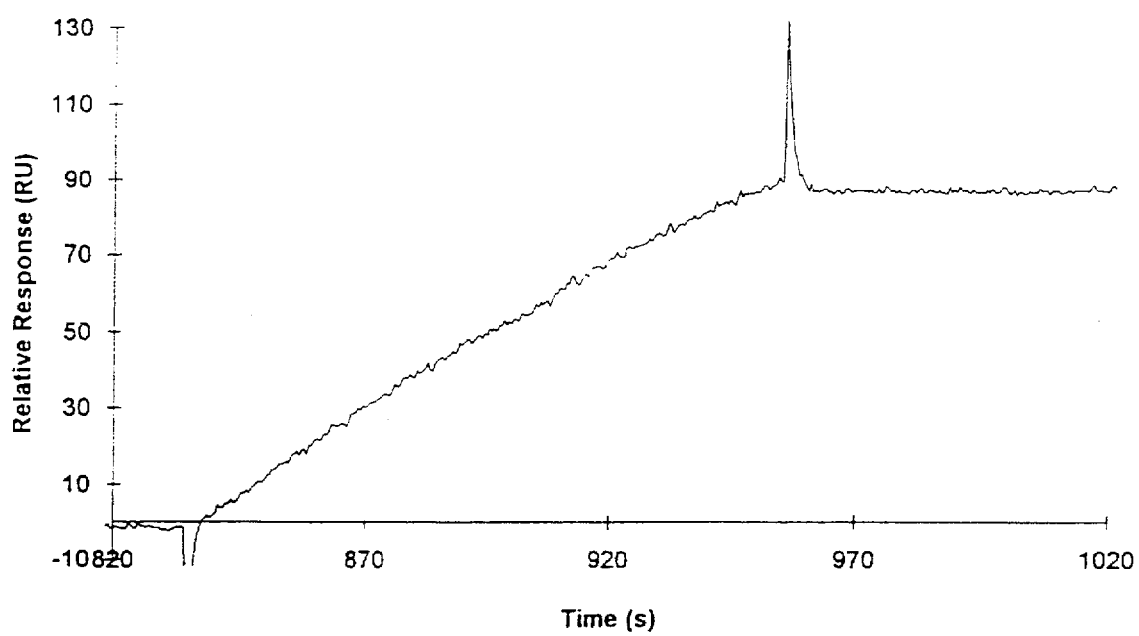
FIG. 1 shows a binding curve for a 60 nM concentration of Mab 7-p24.

Kinetic analysis of the Mab 7-p24 interaction revealed that the system was extremely stable with a dissociation rate constant less than $10^{-5}$ (s$^{-1}$) and that the association rate constant was $2.2 \cdot 10^5$ (M$^{-1}$s$^{-1}$). In order to obtain a reasonable response level for the following competitive experiment, a p24 concentration of 60 nM was chosen. The binding curve for 60 nM concentration is shown in FIG. 1.

Affinity of Synthetic p24 Derived Peptides for Anti-p24 Mab

100 µl volumes of a 60 nM solution of p24 in HBS were mixed with 100 µl of different concentrations (5 nM to 1 mM) of two synthetic p24 derived peptides corresponding to (i) the regions 329–352 (peptide 7): DCKTILKALGPAATL-EEMMTACQG ($M_w$=2494), and (ii) the regions 332–349 (peptide 5): TILKALGPAATLEEMMTA ($M_w$=1841) (obtained from Dr Ake Engström, Department of Immunology, Biomedical Center, University of Uppsala, Sweden). The peptide sequences are according to Ratner et al., Nature 313, 227–284, 1985 and are numbered according to Myers G. et al., Database Human Retroviruses and AIDS, Los Alamos National Laboratory, Los Alamos, U.S.A., 1988. Each mixture was injected at 10 µl/min for two minutes over the sensor surface with captured anti-p24 antibody and the respective binding curves for each peptide were recorded. Peptide 5 was used at the concentrations: 0, 4.91, 14.75, 44.26, 132.78, 398.33, and 1195.00 µM; and peptide 7 at the concentrations 0, 0.005, 0.016, 0.049, 0.147, 0.441, and 1.323 µM.

Figure 2:
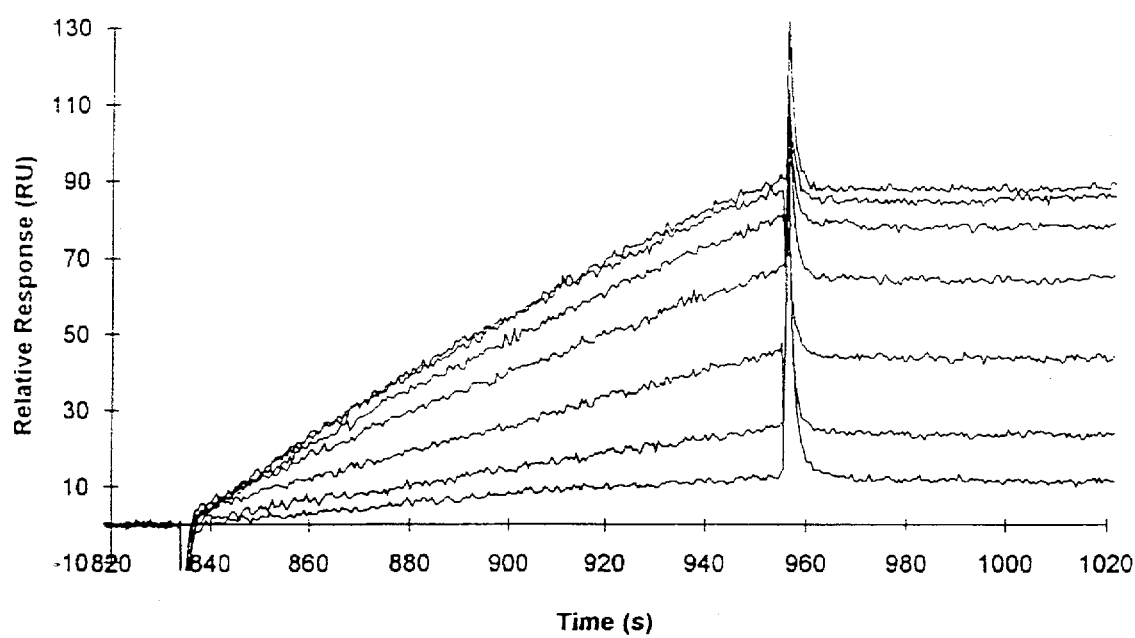
FIG. 2 shows binding curves for peptide 5.
Figure 3:
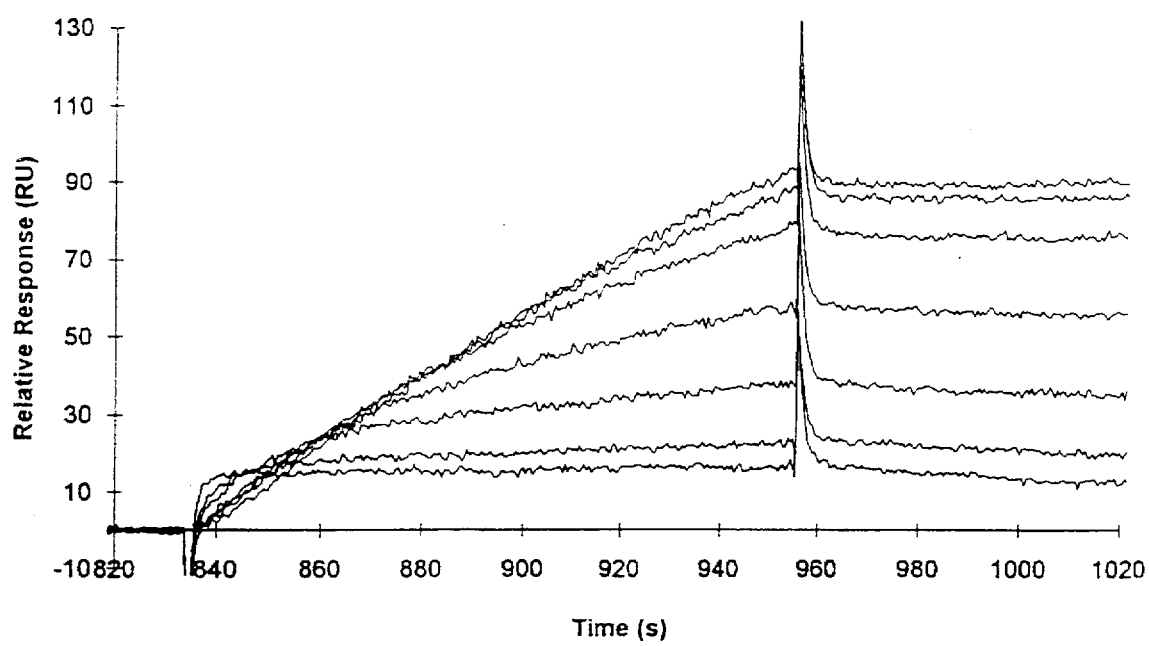
FIG. 3 shows binding curves for peptide 7.
Figure 4:
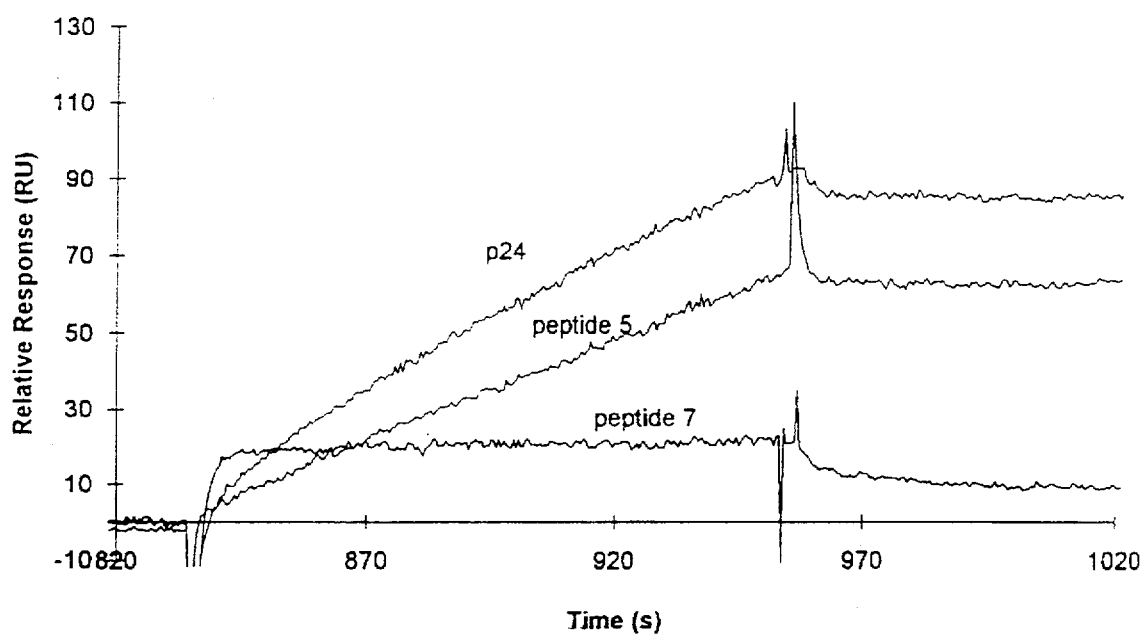
FIG. 4 shows binding curves for peptides 5 and 7.

The binding curves for peptide 5 are shown in overlay plot in FIG. 2, and a corresponding overlay plot of the binding curves for peptide 7 is shown in FIG. 3. FIG. 3 demonstrates that for peptide 7, competing kinetics is seen already at 5 nM concentration, whereas for peptide 5 competition is evident only at µM concentrations, as is seen in FIG. 2. Evidently, these two peptides have quite different affinities for the immobilized antibody. To demonstrate this more directly, p24/peptide mixtures with the two peptides at equal concentrations were injected and the binding curves recorded (p24 at 60 nM and the peptides at 44 µM). The results are shown in FIG. 4 which clearly demonstrates that peptide 7 has a high affinity for the antibody, whereas peptide 5 has a low affinity for the antibody.

EXAMPLE 2

Preparation of Conalbumin-aminotheophylline Conjugate 30.8 mg of conalbumin (Sigma) were dissolved in 0.5 ml PBS-buffer, pH 7.5. 44 µl of a 3.12 mg/ml solution of SPDP (Pharmacia LKB Biotechnology AB, Uppsala, Sweden) in ethanol were added to the protein solution and allowed to react at room temperature for one hour. SPDP-modified conalbumin was transferred into 0.1M acetate buffer, pH 4.5, by buffer exchange on a NAP5-column (Pharmacia LKB Biotechnology AB, Uppsala, Sweden).

6.7 mg of the SPDP-modified conalbumin was reduced with DTE, excess DTE was removed by desalting on a NAP5 column, and the SH-conalbumin preparation was again reacted with SPDP but now at pH 4.5. Excess reagents were removed by desalting on a NAP5 column and 100 µl of a 20 mM aminotheophylline solution was added and allowed to react with the succinimide ester of conalbumin. Excess reagents were again removed by buffer exchange on a NAP column and the conjugate was taken up in 10 mM HBS buffer. The conjugate formed was purified by gel filtration on a Superose™ 12 column (Pharmacia LKB Biotechnology AB, Uppsala, Sweden). A high molecular weight fraction was removed, and the aminotheophylline-conalbumin conjugate was identified by its reaction with immobilised aminotheophylline monoclonal antibody (Kabi Pharmacia AB, Uppsala, Sweden) as detected in the BIAcore™ system. The final yield was 0.15 mg.

Binding of Anti-theophylline Mab to the Sensor Surface and Kinetic Analysis of Conalbumin-aminotheophylline Ligand Interaction A solution of purified monoclonal anti-theophylline antibody (Kabi Pharmacia AB, Uppsala, Sweden) was injected into the BIAcore™ instrument as in Example 1, the anti-theophylline antibody thereby being captured by the immobilised RAMFc. Different solutions of the above prepared conalbumin conjugate varying in concentration from 100 to 1000 nM, were then injected and the binding curves were recorded. Kinetic analysis revealed that the association rate constant was $3.0 \cdot 10^4$ $M^{-1}s^{-1}$ and the dissociation rate constant was $2.2 \cdot 10^{-2}$ $s^{-1}$. For the following competitive experiment, a concentration of 620 nm was chosen, this concentration being close to the $K_D$ ($k_{diss}/k_{ass}$) concentration (730 nM).

Figure 5:
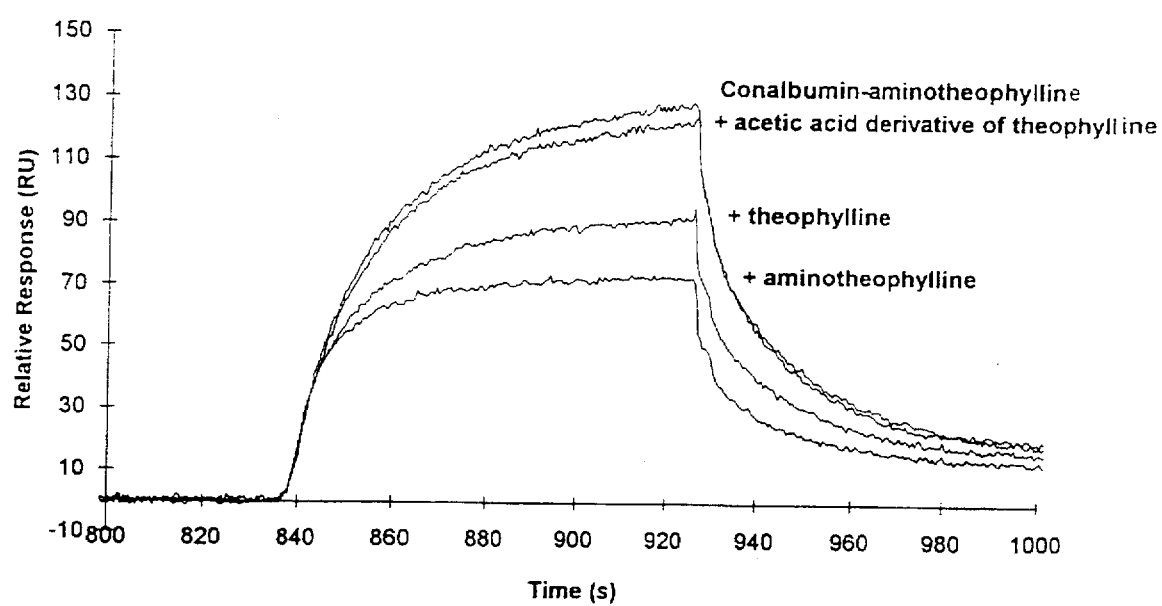
FIG. 5 shows binding curves for theophylline and theophylline derivatives.

Affinity of Theophylline Derivatives for Immobilised Anti-theophylline Monoclonal Antibody 100 µl volumes of a 620 nM solution of the conjugate between aminotheophylline and conalbumin were mixed with each of 100 µl of 500 nM solutions of theophylline (Fluka A.G., Switzerland), 7-theophylline acetic acid (Fluka A.G.) and aminotheophylline (Fluka A.G.), respectively. Each mixture was injected at 10 µl/min for 90 seconds over the surface with captured anti-theophylline monoclonal antibody, and the respective binding curves were recorded. The results are shown in FIG. 5, from which it is evident that aminotheophylline has the highest affinity for the antibody and that the acetic acid derivative of theophylline reacts with much lower affinity. Theophylline itself has an affinity in between.

EXAMPLE 3

Preparation of Conalbumin-histamine Conjugate 6.7 mg of SPDP modified conalbumin, prepared as in Example 2, were reduced with DTE, excess DTE was removed by desalting on a NAP5 column (Pharmacia LKB Biotechnology AB, Uppsala, Sweden) against PBS buffer, and the SH-conalbumin preparation was allowed to react overnight with a six times molar excess of pyridyl-histamine derivative (Kabi Pharmacia AB, Uppsala, Sweden). The conalbumin-histamine conjugate was purified and tested for binding activity as described above. The final yield of purified conjugate was 1.5 mg.

Binding of Anti-histamine Mab to the Sensor Surface and Kinetic Analysis of Conalbumin-histamine Ligand Interaction A solution of purified monoclonal anti-histamine antibody (Kabi Pharmacia AB, Uppsala, Sweden) was injected into the BIAcore™ instrument as in Example 1, the anti-histamine antibody thereby being captured by the immobilised RAMFc. Different solutions of the above prepared conalbumin conjugate, varying in concentration from 100 to 1000 nM, were then injected and the binding curves were recorded. Kinetic analysis gave an association rate constant ($k_{ass}$) value of $2.1 \cdot 10^4$ $M^{-1}s^{-1}$ for the association of the histamine conjugate to the immobilised anti-histamin antibody, and a dissociation rate constant ($k_{diss}$) for the dissociation of the histamin conjugate from the immobilised anti-histamin antibody of $4.3 \cdot 10^{-4}$ $s^{-1}$, i.e. substantially lower than for the theophylline conjugate in Example 2. For the following competitive experiment, a concentration of 80 nM was chosen.

Figure 6:
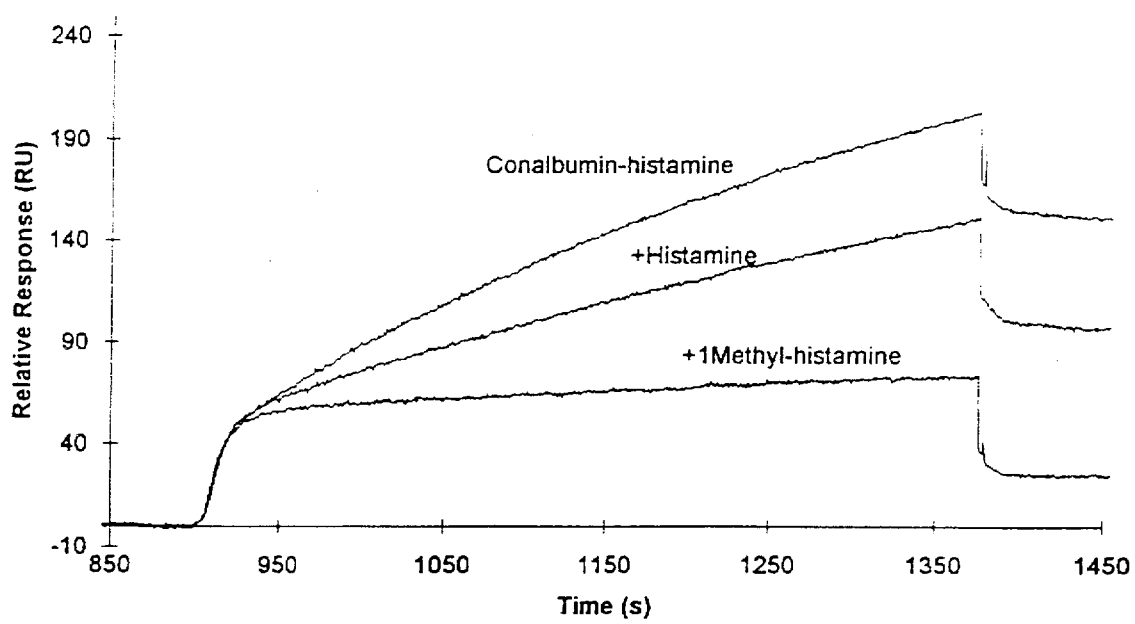
FIG. 6 shows binding curves for histamine and histamine derivatives.

Affinity of Histamine and Methylhistamine for Immobilised Anti-histamine Monoclonal Antibody 100 µl volumes of a 80 nM solution of the conjugate between histamine and conalbumin were mixed with each of 100 µl of 220 nM solutions of histamine (Sigma, St. Louis, Mo., U.S.A.) and methylhistamine, respectively. Each mixture was injected at 10 µl/min for 8 minutes over the surface with captured anti-histamine monoclonal antibody, and the respective binding curves were recorded. The results are shown in FIG. 6, from which it is evident that methylhistamine has a higher affinity for the antibody than histamine itself.

I claim:

1. A method of determining the affinity and kinetic properties of low molecular weight ligands for their interaction with a binding site of a common receptor, comprising the steps of:

immobilizing a receptor on a sensing surface of a mass sensing device;

preparing two or more mixtures comprising known proportions of a low molecular weight ligand and a ligand analogue, wherein the response of the ligand analogue binding on the sensing surface is at least about 20 times greater than that of the low molecular weight ligand;

separately contacting said two or more mixtures with the sensing surface, under conditions which allow interaction between the binding site of the receptor and the ligand and ligand analogue, and measuring the response; and comparing the response of each of said two or more mixtures with that of the ligand analogue alone, wherein the distortion of the ligand analogue response is representative of the affinity and kinetic properties of the ligand.

2. The method of claim 1, wherein the ligand analogue is a high molecular weight molecule.

3. The method of claim 1 or 2, wherein said measured response is shown by recording a partial binding curve (response vs time) for the ligand analogue and each mixture, respectively.

4. The method of claim 3, wherein the interaction of the receptor and the ligand or ligand analogue leads to equilibrium causing the binding curve to reach an equilibrium state.

5. The method of claim 3, wherein the binding curve is an association/dissociation curve.

6. The method of claim 1, wherein the concentration of the ligand analogue is selected close to a dissociation constant ($K_D$) concentration of the ligand analogue.

7. The method of claim 1, wherein said mass sensing device is one based upon evanescent wave sensing.

8. The method of claim 7, wherein said evanescent wave sensing is based on surface plasmon resonance.

9. The method of claim 1 or 2, wherein said low molecular ligands are potential drugs.

10. The method according to claim 3, wherein the high molecular weight ligand reacts in a one-to-one fashion with the immobilized receptor, wherein the interaction has a dissociation rate constant of between 0.001 and 0.1.

11. The method according to claim 3, wherein the response is measured during at least the part of the reaction which corresponds to the initial part of the binding curve.

12. The method according to claim 11, wherein the measurement of the response is terminated prior to the reaction reaching steady state.

* * * * *